United States Patent [19]

Zuckerwar

[11] Patent Number: 4,478,069
[45] Date of Patent: Oct. 23, 1984

[54] FLOW RESISTIVITY INSTRUMENT IN THE EARTH

[75] Inventor: Allan J. Zuckerwar, Newport News, Va.

[73] Assignee: The United States of America as represented by the Administrator of the National Aeronautics and Space Administration, Washington, D.C.

[21] Appl. No.: 508,372

[22] Filed: Jun. 27, 1983

[51] Int. Cl.³ .............................................. G01N 15/08
[52] U.S. Cl. .......................................... 73/38; 73/155
[58] Field of Search ............................ 73/38, 594, 155

[56] References Cited

U.S. PATENT DOCUMENTS

| | | |
|---|---|---|
| 3,172,285 | 3/1965 | Dietert et al. ........................... 73/38 |
| 3,861,196 | 1/1975 | Domenighetti ......................... 73/38 |
| 3,889,521 | 6/1975 | Jakimowicz . | 
| 3,924,463 | 12/1975 | Urbanosky . |
| 3,996,788 | 12/1976 | Purves . |

FOREIGN PATENT DOCUMENTS 534148 12/1954 Belgium .
737523 7/1943 Fed. Rep. of Germany .
779859 11/1980 U.S.S.R. .

*Primary Examiner*—Howard A. Birmiel
*Attorney, Agent, or Firm*—Howard J. Osborn; John R. Manning; William H. King

[57] ABSTRACT

Method and apparatus for making in-situ measurements of flow resistivity on the Earth's ground surface. The novel feature of the invention is two concentric cylinders, 22 and 23, inserted into the ground surface 24 with a measured pressure 21 applied to the surface inside the inner cylinder 22. The outer cylinder 23 vents a plane B-B beneath the surface to the atmosphere through an air space 28. The flow to the inner cylinder is measured (16) thereby indicating the flow from the surface to the plane beneath the surface.

6 Claims, 2 Drawing Figures

FLOW RESISTIVITY INSTRUMENT IN THE EARTH

ORIGIN OF THE INVENTION

The invention described herein was made by an employee of the United States Government and may be manufactured and used by or for the Government for governmental purposes without the payment of any royalties thereon or therefor.

BACKGROUND OF THE INVENTION

The invention relates to a method and apparatus for making in-situ measurements of the flow resistivity on the Earth's ground surface.

"Flow resistivity" is defined as the ratio of the pressure gradient across a test specimen to the volume of air flowing through the specimen per unit time. Because the flow resistivity is an important parameter appearing in many acoustical models of the Earth's ground surface, it is desirable to accompany measurements of acoustic ground impedance with measurements of flow resistivity.

Prior art resistivity instruments universally are comprised of four parts: an air supply or vacuum, one or more flow meters, one or more differential pressure measuring devices, and a specimen holder. The specifications on such instruments are given in ASTM Designation C522-80, "Standard Test Method for Airflow Resistance of Acoustical Materials."

The disadvantage of the prior art flow resistivity instruments is they are intrusive; that is, they require that a test specimen be removed from the bulk material for placement in a specimen holder. In the case of ordinary acoustical materials, which are generally chemically stable, removal of a specimen from the bulk does not affect its flow properties. In the case of the Earth's ground surface, however, removal of a specimen from the ground causes immediate and irreversible changes therein: loss of volatile matter, especially moisture; changes in texture; changes in organic content; and partial or total destruction of the root system of surface vegetation.

It is therefore the primary object of this invention to provide a method and apparatus for making in-situ measurements of the flow resistivity on the Earth's ground surface.

Other objects and advantages of this invention will become apparent hereinafter in the specification and drawings.

SUMMARY OF THE INVENTION

The invention is a method and apparatus for measuring the flow resistivity on the Earth's ground surface. The method includes the steps of subjecting a section of the Earth's ground surface to an air pressure P from an air supply; venting to the atmosphere a cross-sectional area S of the subterrain at a depth of H from the section of the Earth's surface under test; measuring the volume velocity U of air flow to the section of the Earth's surface under test to obtain the air flow to said subterranean area; and computing the flow resistivity R from the formula:

$$R = PSC/UH$$

where C is a correction factor.

The apparatus that constitutes the invention is a specimen holder which is adapted to make in-situ flow resistivity measurements of the Earth's ground surface. A first inner cylinder with a cross-sectional area S is adapted to receive an air pressure into one of its ends and adapted to penetrate the Earth's surface at its other end. A second outside cylinder concentric with the first cylinder also penetrates the ground. A recess on the inside surface of the outer cylinder creates an air space between the two cylinders whenever they penetrate the ground surface. A series of holes in the part of the outer cylinder that does not penetrate the ground surface vents the air space to the atmosphere. Consequently, the subterrain at the penetrating end of the first cylinder is vented to the atmosphere. The flow of air through the first cylinder and through the air space to the atmosphere is the measure of the volume velocity U.

DETAILED DESCRIPTION OF THE INVENTION

Figure 1:
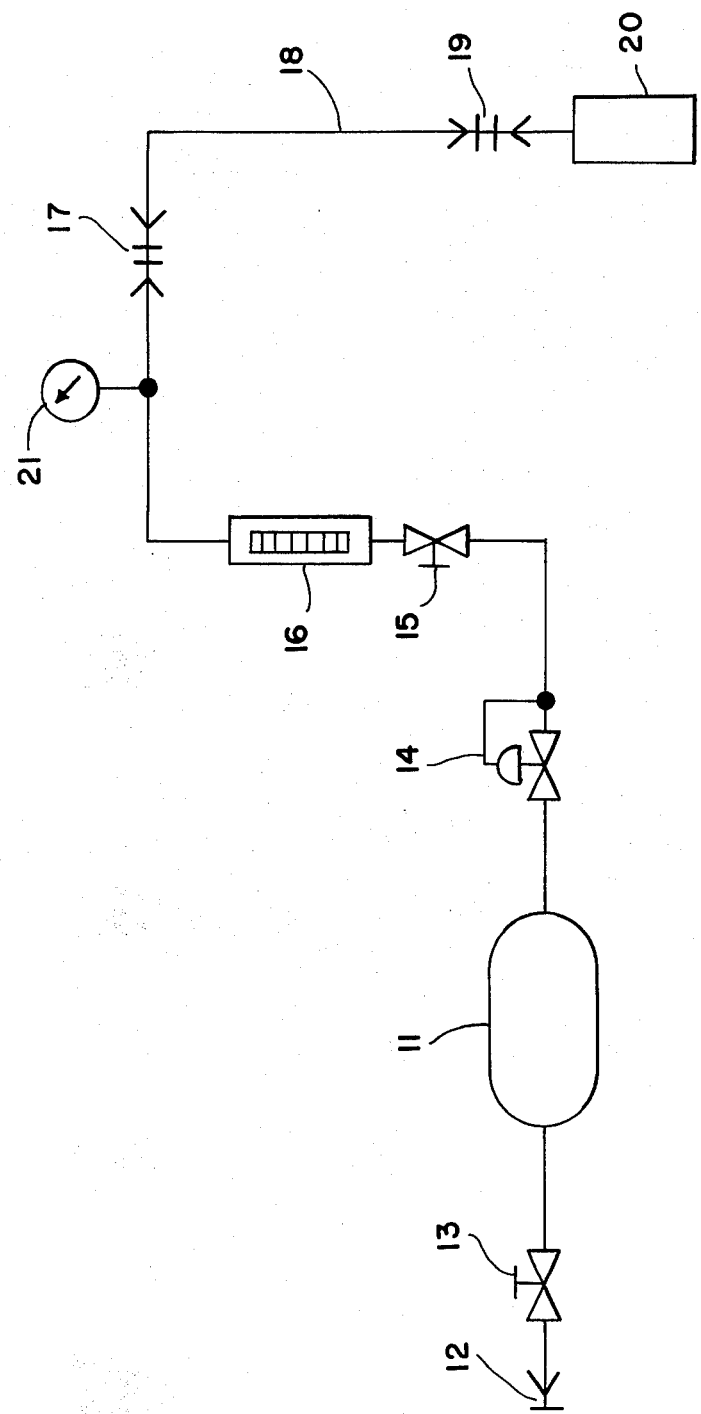
FIG. 1 is a block diagram of the invention.

Turning now to the embodiment of the invention selected for illustration in the drawing the number 11 in FIG. 1 designates a compressed air reservoir which is initially charged with compressed air through a quick connect 12 and shut off valve 13. During a flow resistivity measurement air flows from reservoir 11 through a pressure regulator 14, a shut off valve 15, a flow meter 16, a quick connect 17, a flexible hose 18, and a quick connect 19 into a specimen holder 20. The flow meter 16, which may be of the "rotameter" type, measures the volume velocity U of the air flow. A pressure gage 21 with a "bourdon" tube, measures the pressure at the inlet of the specimen holder 20 and thus at the upper surface of the specimen. The rotameter and dial gage do not require electricity for their operation and are especially convenient for deployment in the field.

Figure 2:
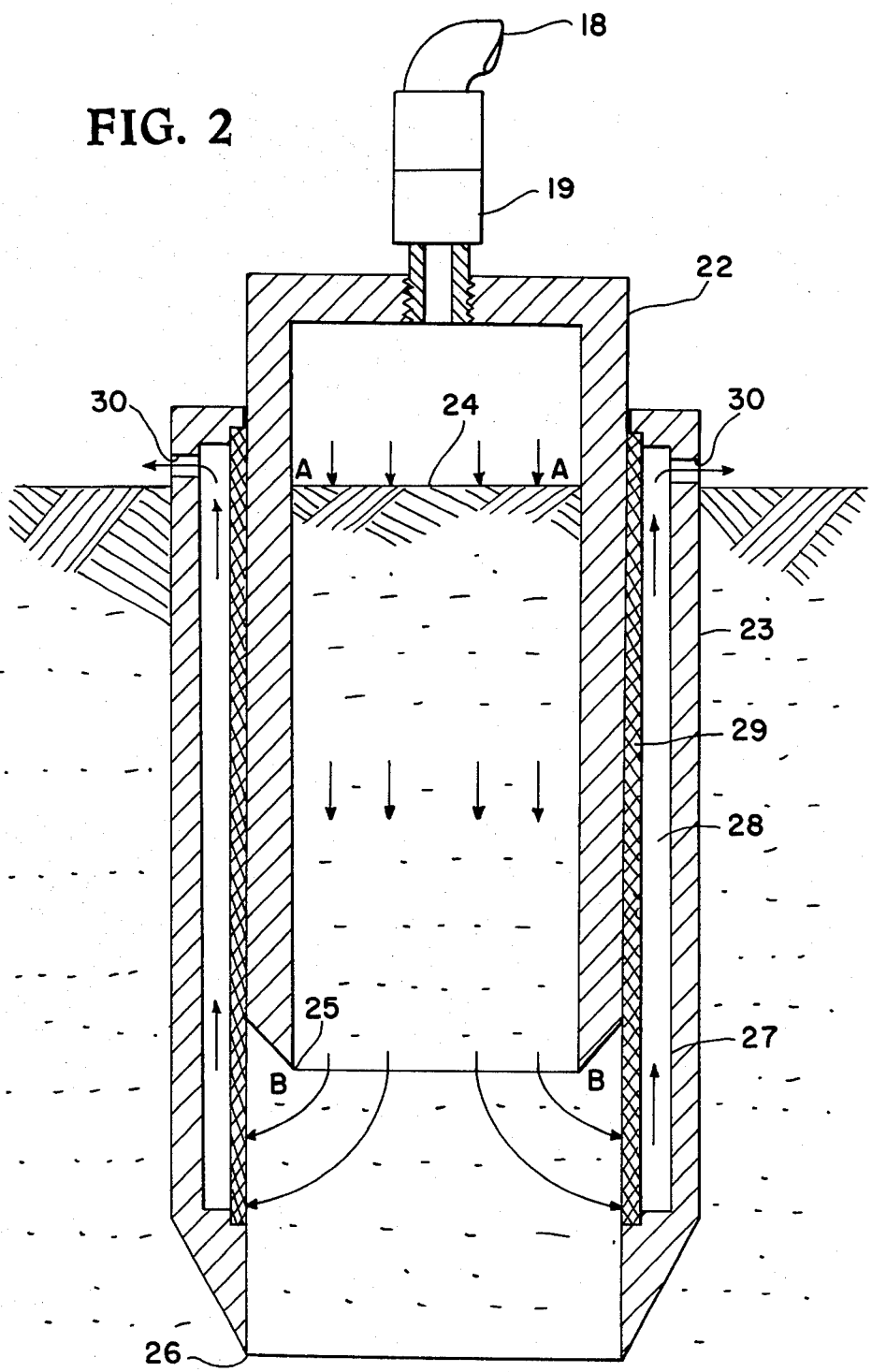
FIG. 2 is a schematic drawing of the specimen holder shown in FIG. 1.

The specimen holder 20 shown in detail in FIG. 2 is the novel component of the invention. It consists of two concentric cylinders, an inner cylinder 22 and an outer cylinder 23, both made of a sturdy material like stainless steel. The specimen of ground 24 under test is contained within the inner cylinder. The function of this arrangement is to make the air pressure at the upper surface A—A of the specimen equal to the pressure measured on pressure gage 21, and the pressure at the lower surface B—B approximately equal to the ambient pressure.

Inner cylinder 22 is adapted at one of its ends to connect to the air pressure by means of the quick connect 19 and is adapted at its other end by means of a knife edge 25 to be driven into the Earth's surface. Outer cylinder 23 has an inside diameter equal to the outside diameter of inner cylinder 22 and is adapted at one of its ends by means of a knife edge 26 to be driven into the Earth's surface. An annular recess 27 is formed on the inside surface of the outer cylinder such that when the outer cylinder penetrates the Earth's surface a trench or air space 28 is formed between the inner and outer cylinders.

The inner cylinder 22 is driven into the ground 24 first, with the aid of a cap (not shown) especially made to bear the blows of a hammer or other instrument, to a typical depth of six inches. A small portion of the inner cylinder remains above the surface. A knife edge 25 facilitates its penetration into the ground. Then the concentric outer cylinder 23 is driven into the ground, also with the aid of a specially made cap (not shown) which clears the inner cylinder. The outer cylinder penetrates the ground several inches beyond the inner cylinder. A knife edge 26 at the bottom of the outer cylinder and recess 27 form an annular trench 28 about the inner cylinder. The interior surface of the outer cylinder consists of a rigid, firmly fastened cylindrical screen 29, which slides along the inner cylinder as the outer cylinder is driven into the ground. The screen prevents the ground material below the inner cylinder from falling into the trench. A series of holes 30, drilled into the wall of the outer cylinder and located above the ground surface, permits the passage of air from the trench to the ambient atmosphere and ensures that the pressure throughout the trench will remain at ambient pressure.

After the two cylinders are properly positioned, the air supply is connected to the inner cylinder through quick connect 19. A uniform flow is established in the ground specimen between planes A—A and B—B. The pressure at B—B, because of the close proximity of this plane to the trench, is approximately equal to the ambient pressure. After the flow passes plane B—B, it turns radially toward the trench and passes upward through the trench and through the vent holes 30. The flow through the specimen holder is indicated by the arrows in the figure. The pressure drop between plane B—B and the trench is actually very small and can be corrected for as shown in the formulas given below.

To prevent the pressurized air from changing the position of the inner cylinder relative to the outer cylinder, an arrangement can be made to fasten the inner cylinder to the ground or to the outer cylinder after the two cylinders are in place. One such arrangement is to place pins in two of the holes 30 in the outer cylinder to serve as anchors for a retaining wire tightly stretched across the top of the inner cylinder.

The flow resistivity R is determined from the formula $R = PSC/UH$, where P is the pressure as read on pressure gage 21, S is the cross-sectional area of the ground specimen, U is the volume velocity of the air flow as measured on flow meter 16, H is the depth of the specimen (distance between planes A—A and B—B), and C is a correction factor to account for the pressure drop between plane B—B and the trench: $C = 1 - 0.324a/H$, where a is the internal radius of the inner cylinder.

The advantage of this invention is it is nonintrusive and thus permits in-situ measurements on a ground surface in its natural condition. Changes in flow properties of a test specimen due to its removal from the ground are eliminated.

An alternate embodiment of the invention is the specimen holder could be dimensioned to make the radial flow, instead of the axial (vertical) flow, the more significant part of the flow through the specimen. This feature could be significant in studies of anisotropic properties of flow resistivity.

What is claimed is:

1. A method for measuring the air flow resistivity on the Earth's ground surface comprising the steps of:
   subjecting a section of the Earth's ground surface to an air pressure P from an air supply;
   venting to the atmosphere a cross-section S of the subterrain plane at a depth of H from said section of the Earth's surface; and
   measuring the volume velocity U of air flow to said section to obtain the air flow from said section of the Earth's surface to said subterranean plane.

2. A method for measuring the air flow resistivity on the Earth's ground surface according to claim 1 including the step of computing the flow resistivity R from the formula:

$$R = PSC/UH$$

where C is a correction factor.

3. Apparatus for measuring the air flow resistivity on the Earth's surface comprising:
   means for subjecting a section of the Earth's surface to an air pressure;
   means for venting to the atmosphere a cross-sectional area of a subterrain plane directly below said section of the Earth's surface; and
   means for measuring the flow of air to said section to thereby obtain a measurement of the flow of air from said section of the Earth's surface to said subterrain plane.

4. Apparatus for measuring the air flow resistivity on the Earth's surface according to claim 3 wherein said means for venting to the atmosphere the subterrain plane directly below said section comprises:
   a first inner cylinder with a first end enclosed and adapted to receive said air pressure and with a second end adapted to penetrate the Earth's surface to said plane thereby enclosing said enclosed area; and
   a second concentric outer cylinder with an inside diameter equal to the outside diameter of said first cylinder, with one of its ends adapted to penetrate the Earth's surface several inches beyond the penetration of the first cylinder, a recess in the inner surface of said second cylinder extending from below said plane to above the Earth's surface such that whenever said second cylinder penetrates the Earth's surface beyond the penetration of the first cylinder an air space is formed between the first and second cylinders, and a series of holes in the upper part of the second cylinder for venting the air in said air space into the atmosphere.

5. Apparatus according to claim 4 including a layer of material covering said recess which blocks earth from getting into the recess but allows air to flow into the recess.

6. Apparatus according to claim 5 wherein said layer of material is screen.

* * * * *